(12) United States Patent
Cobb

(10) Patent No.: US 9,375,172 B2
(45) Date of Patent: Jun. 28, 2016

(54) APPARATUS FOR SUBSTANCE DETECTION

(71) Applicant: CORNING INCORPORATED, Corning, NY (US)

(72) Inventor: Joshua Monroe Cobb, Victor, NY (US)

(73) Assignee: Corning Incorporated, Corning, NY (US)

( * ) Notice: Subject to any disclaimer, the term of this patent is extended or adjusted under 35 U.S.C. 154(b) by 324 days.

(21) Appl. No.: 13/664,826

(22) Filed: Oct. 31, 2012

(65) Prior Publication Data

US 2014/0117254 A1 May 1, 2014

Related U.S. Application Data

(60) Provisional application No. 61/556,468, filed on Nov. 7, 2011.

(51) Int. Cl.
*A61B 5/1455* (2006.01)
*G01N 21/64* (2006.01)
*A61B 5/145* (2006.01)
(Continued)

(52) U.S. Cl.
CPC ......... *A61B 5/14556* (2013.01); *A61B 5/14532* (2013.01); *G01J 3/021* (2013.01); *G01J 3/0208* (2013.01); *G01J 3/0218* (2013.01); *G01J 3/0229* (2013.01); *G01J 3/4406* (2013.01); *G01N 21/645* (2013.01); *G01N 2021/6421* (2013.01); *G01N 2021/6471* (2013.01); *G01N 2201/0639* (2013.01)

(58) Field of Classification Search
CPC . A61B 5/14556; A61B 5/14532; G01J 3/021; G01J 3/0229; G01J 3/0208; G01J 3/0218; G01J 3/4406; G01N 21/645; G01N 2021/6421; G01N 2021/6471; G01B 2201/0639

USPC .......................................... 359/583, 587, 586
See application file for complete search history.

(56) References Cited

U.S. PATENT DOCUMENTS 4,806,750 A 2/1989 Vincent
4,870,268 A 9/1989 Vincent et al.
(Continued)

OTHER PUBLICATIONS

Judge et al; "Continuous Glucose Monitoring Using a Novel Glucose/Galactose Binding Protein: Results of a 12 Hour Feasibility Study With the Becton Dickinson Glucose/Galactose Binding Protein Sensor"; Diabetes Technology & Therapeutics, vol. 13 No. 3 2011.

(Continued)

*Primary Examiner* — Yara B Green
(74) *Attorney, Agent, or Firm* — Kevin L. Bray

(57) ABSTRACT

A sensing apparatus for detecting light of first and second fluorescent wavelength bands has a light source to generate an excitation wavelength to a first collimator element. A dichroic multiplexer has a first coated surface oblique to the optical axis and treated to transmit the excitation wavelength and to reflect the second fluorescent wavelength band and a second coated surface treated to transmit the excitation wavelength and the second fluorescent wavelength band and to reflect the first fluorescent wavelength band. A focusing element focuses the excitation light toward a light guide and directs collimated light of the first and second fluorescent wavelength bands from the light guide to the dichroic multiplexer. A first detector element is in the path of reflected light of the first fluorescent wavelength band and a second detector element is in the path of reflected light of the second fluorescent wavelength band.

20 Claims, 10 Drawing Sheets

(51) Int. Cl.
*G01J 3/44* (2006.01)
*G01J 3/02* (2006.01)

(56) References Cited

U.S. PATENT DOCUMENTS

| | | | | |
|---|---|---|---|---|
| 4,977,319 A | * | 12/1990 | Supernaw | 250/255 |
| 5,009,230 A | | 4/1991 | Hutchinson | |
| 5,319,399 A | * | 6/1994 | Hudgins | 351/222 |
| 5,456,252 A | * | 10/1995 | Vari et al. | 600/301 |
| 5,574,811 A | | 11/1996 | Bricheno et al. | |
| 5,786,915 A | * | 7/1998 | Scobey | 398/82 |
| 5,920,347 A | * | 7/1999 | Aoki | 348/339 |
| 6,836,678 B2 | | 12/2004 | Tu | |
| 7,263,394 B2 | | 8/2007 | Wang | |
| 7,949,382 B2 | | 5/2011 | Jina | |
| 8,027,041 B1 | * | 9/2011 | Mitchell et al. | 356/456 |
| 2004/0222384 A1 | * | 11/2004 | Lee et al. | 250/458.1 |
| 2005/0231715 A1 | | 10/2005 | Horigome et al. | |
| 2007/0107769 A1 | | 5/2007 | Cobb et al. | |
| 2009/0086314 A1 | * | 4/2009 | Namba et al. | 359/383 |
| 2009/0201490 A1 | | 8/2009 | Gerlitz | |
| 2009/0285761 A1 | * | 11/2009 | Wang et al. | 424/9.6 |
| 2011/0205501 A1 | | 8/2011 | Cobb | |

OTHER PUBLICATIONS

Weidemaier et al; "Multi-Day Pre-Clinical Demonstration of Glucose/Galactose Binding Protein-Based Fiber Optic Sensor"; Biosensors and Bioelectronics; 2011; 7 Pages.

* cited by examiner

APPARATUS FOR SUBSTANCE DETECTION

CROSS REFERENCE TO RELATED APPLICATIONS

This application claims the benefit of U.S. Provisional Patent Application Ser. No. 61/556,468, filed on Nov. 7, 2011, entitled "APPARATUS FOR SUBSTANCE DETECTION" in the name of Joshua M. Cobb, the contents of which are incorporated fully herein by reference.

FIELD OF THE INVENTION

This invention generally relates to light sensing apparatus and more particularly relates to apparatus and methods for providing excitation light to a sample and sensing fluorescent light of different wavelengths from the sample.

BACKGROUND

The fluorescence of various chemical substances when subjected to light energy can provide useful information and has broad applications in a number of fields, including medical and dental imaging, microscopy, and non-destructive testing, for example. In fluorescence imaging, light of a first wavelength band is emitted and directed toward a sample that contains a fluorophore or other type of fluorescing agent. The fluorescing material may occur naturally; for example, teeth and bones are known to fluoresce when excited with light energy at various wavelengths. Alternately, one or more fluorescing agents may be introduced to the sample, such as by injection or coating, for example. The fluorescing substance emits light of a second wavelength band in response to the emitted excitation light. A sensing apparatus isolates the fluorescent light from the emitted excitation light according to wavelength. The amount and spectrum of light that is sensed provides an indicator of the composition of the sample material. In the optical system of the sensing apparatus, one or more optical filters are generally used for separating low-level fluorescent light of the second wavelength band from the higher-energy emitted light of the first wavelength band.

The schematic view of FIG. 1 shows a conventional optical apparatus 10 for fluorescence sensing. A light source 12 emits the excitation light of the first wavelength band toward a beamsplitter 20. Beamsplitter 20 directs this light toward a sample 30. Fluorescent light from sample 30 is then transmitted back through beamsplitter 20 and along a detection path to a detector 22. An excitation filter 24 blocks unwanted light from the excitation light path. An emission filter 26 blocks unwanted light from the detection path. Lenses 18 and other optical components are provided for conditioning the light path as needed.

Among difficulties with the conventional approach is the need for precision alignment of beamsplitter 20 and other components, with little tolerance for positioning error. As a further drawback, emission and detection light paths are orthogonal to each other, which makes it difficult to design optical apparatus 10 as a compact device. Because the fluorescent signal is much weaker than the emitted light energy, noise is a problem. Using high levels of excitation energy can add to this problem, since unwanted fluorescence can occur from other sources, such as from lenses and other components in the optical system itself. This type of "stray" fluorescence can be particularly difficult to suppress from the detection path. In light of these problems, apparatus of this type can require costly components and fabrication in order to reduce inherent noise and achieve needed performance levels.

Fluorescence sensing is even more challenging where fluorescence occurs at multiple wavelengths. The use of multiple fluorophores in a single sample, for example, has been shown to be of value in a number of applications. Glucose monitoring is one application in which multiple fluorophores can be used, wherein the ratio of fluorescence at two different wavelengths bands can be used to help monitor concentration levels in a sample, such as in a patient's skin tissue.

Thus, it can be seen that there is a need for a fluorescence sensing apparatus that is compact, that has reduced requirements for component alignment and cost, and that provides an improved signal-to-noise ratio for detecting fluorescent energy at multiple wavelengths.

SUMMARY

The present invention addresses the need for fluorescence sensing that is capable of detecting fluorescence emission at multiple wavelengths. The present invention provides a sensing apparatus for detecting light of a first fluorescent wavelength band and light of a second fluorescent wavelength band from a sample, the apparatus comprising:
  a light source energizable to generate a light of an excitation wavelength and disposed along an optical axis in a first focal region of a first collimator element; a dichroic multiplexer formed on a transparent substrate and comprising:
    (i) a first coated surface oblique to the optical axis and treated to transmit light of the excitation wavelength and to reflect light of at least the second fluorescent wavelength band;
    (ii) a second coated surface spaced apart from the first coated surface and treated to transmit light of the excitation wavelength and of the second fluorescent wavelength band and to reflect light of the first fluorescent wavelength band;
  a focusing element disposed to focus the light of the excitation wavelength toward a light guide and to direct collimated light of the first fluorescent wavelength band and collimated light of the second fluorescent wavelength band from the light guide to the dichroic multiplexer;
  a first detector element in the path of reflected light of the first fluorescent wavelength band from the second coated surface; and
  a second detector element in the path of reflected light of the second fluorescent wavelength band from the first coated surface.

From an alternate aspect, the present invention provides a glucose level sensing apparatus comprising:
  a light source energizable to generate a light of an excitation wavelength and disposed along an optical axis in a first focal region of a first collimator element;
  a dichroic multiplexer formed on a transparent substrate and comprising:
    (i) a first coated surface oblique to the optical axis and treated to transmit light of the excitation wavelength and to reflect light of at least the second fluorescent wavelength band;
    (ii) a second coated surface parallel to the first coated surface and treated to transmit light of the excitation wavelength and of the second fluorescent wavelength band and to reflect light of the first fluorescent wavelength band;
  a focusing element disposed to focus the light of the excitation wavelength toward a light guide to the sample and to direct collimated light of the first fluorescent wavelength band and collimated light of the second fluorescent wavelength band from the light guide to the dichroic multiplexer;

a first detector element in the path of reflected light of the first fluorescent wavelength band from the second coated surface;

a second detector element in the path of reflected light of the second fluorescent wavelength band from the first coated surface; and a control logic processor in signal communication with the light source and with the first and second detector elements and further in signal communication with a display device for displaying a result according to measurements from the first and second detector elements.

Advantageously, embodiments of the present invention provide a compact solution to the fluorescence imaging problem, with reduced requirements for alignment of optical components. The arrangement of components that is used helps to reduce crosstalk and noise effects, while using a small number of light-conditioning components.

These and other aspects, objects, features and advantages of the present invention will be more clearly understood and appreciated from a review of the following detailed description of the preferred embodiments and appended claims, and by reference to the accompanying drawings.

DETAILED DESCRIPTION

Figure 1:
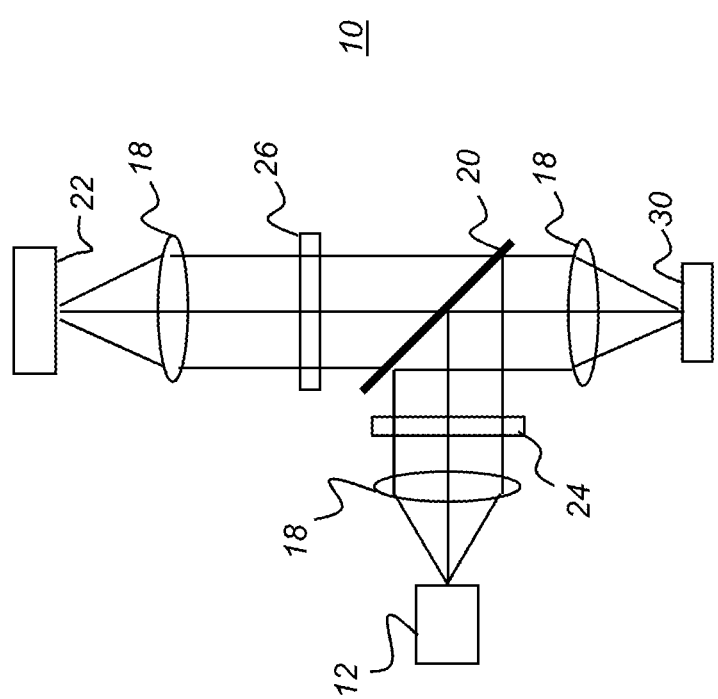
FIG. 1 is a schematic view that shows a conventional fluorescence detection apparatus.

It is to be understood that elements not specifically shown or described may take various forms well known to those skilled in the art. Figures shown and described herein are provided in order to illustrate key principles of operation and component relationships along their respective optical paths according to the present invention and are not drawn with intent to show actual size or scale. Some exaggeration may be necessary in order to emphasize basic structural relationships, function, or principles of operation. Some conventional components that would be needed for implementation of the described embodiments, such as various types of optical mounts, for example, are not shown in the drawings in order to simplify description of the invention itself. In the drawings and text that follow, like components are designated with like reference numerals, and similar descriptions concerning components and arrangement or interaction of components already described are omitted.

Where they are used, the terms "first", "second", and so on, do not necessarily denote any ordinal or priority relation, but may be simply used to more clearly distinguish one element from another.

As used herein, the term "energizable" relates to a device or set of components that perform an indicated function upon receiving power and, optionally, upon receiving an enabling signal. The term "fluorescent" relates to light that is generated as a fluorescence response to an excitation light source in a sensing apparatus. In subsequent description, the focal region for an optical element is considered to be the spatial zone or vicinity of highest light concentration from that element.

Light is considered to be incident on a surface when it is either reflected from that surface or when it transits, or passes through, the surface. References to coatings and coated surfaces may refer to dichroic optical coatings, formed from multiple thin-film layers of material deposited on a substrate to form a treated surface that is designed to provide a desired spectral characteristic, selectively transmitting or reflecting various wavelengths, using filter fabrication techniques well known in the optical coatings art. In the context of the present disclosure, a coating is considered to transmit or be transmissive at a wavelength when it transmits at least about 60 percent, preferably more than 80 percent of light having that wavelength. Similarly, a coating is considered to reflect or to be reflective at a wavelength when it reflects at least about 60 percent, preferably more than 80 percent of light having that wavelength. In general, for embodiments of the present invention described subsequently, higher levels of reflectivity and transmission for the intended wavelength bands from coated surfaces result in improved performance and more accurate measurement. The term "pixel" or picture element has its conventional meaning, relating to a sensor or group of sensors typically arranged within an array for providing a signal according to the intensity of incident light.

The term "oblique", as used in the present disclosure, describes an angular relationship that is not parallel or normal, that is, other than an integer multiple of 90 degrees. In practice, two optical surfaces are considered to be oblique with respect to each other if they are offset from parallel or normal by at least about +/−2 degrees or more. Similarly, a line and a plane are considered to be oblique to each other if they are offset from parallel or normal by at least about +/−2 degrees or more. Substantially parallel planes are parallel to within +/−2 degrees. Likewise, substantially parallel beams are parallel to within about +/−2 degrees.

The term "wavelength band" relates to a narrow range of wavelengths about a central wavelength. In the context of the present disclosure, the wavelength band for emitted light used for excitation is typically no larger than about +/−20 nm about a central wavelength. The wavelength bands for fluorescent light from the illuminated sample are typically larger and may extend over a range of about +/−40 nm. In the context of the present disclosure, the abbreviated term "wavelength" may be used to more generally indicate a particular wavelength band.

Embodiments of the present invention take advantage of a novel arrangement of filter surfaces to direct light of different wavelengths to the appropriate destination in a compact detection apparatus, while reducing noise and crosstalk effects. Embodiments of the present invention are suitable for applications that include glucose monitoring and other uses in which excitation of the sample substances by light energy causes fluorescent emission over different wavelength bands, and wherein it is useful to separate and measure the light from each individual fluorescent wavelength band.

By collimated light is meant light for which the conjugate image location is at or near infinity. A divergence angle can be introduced by having an extended object source, but if this source is small when compared to the focal length of the lens, then the light is substantially parallel. In practice, collimated light neither converges nor diverges appreciably.

Figure 2:
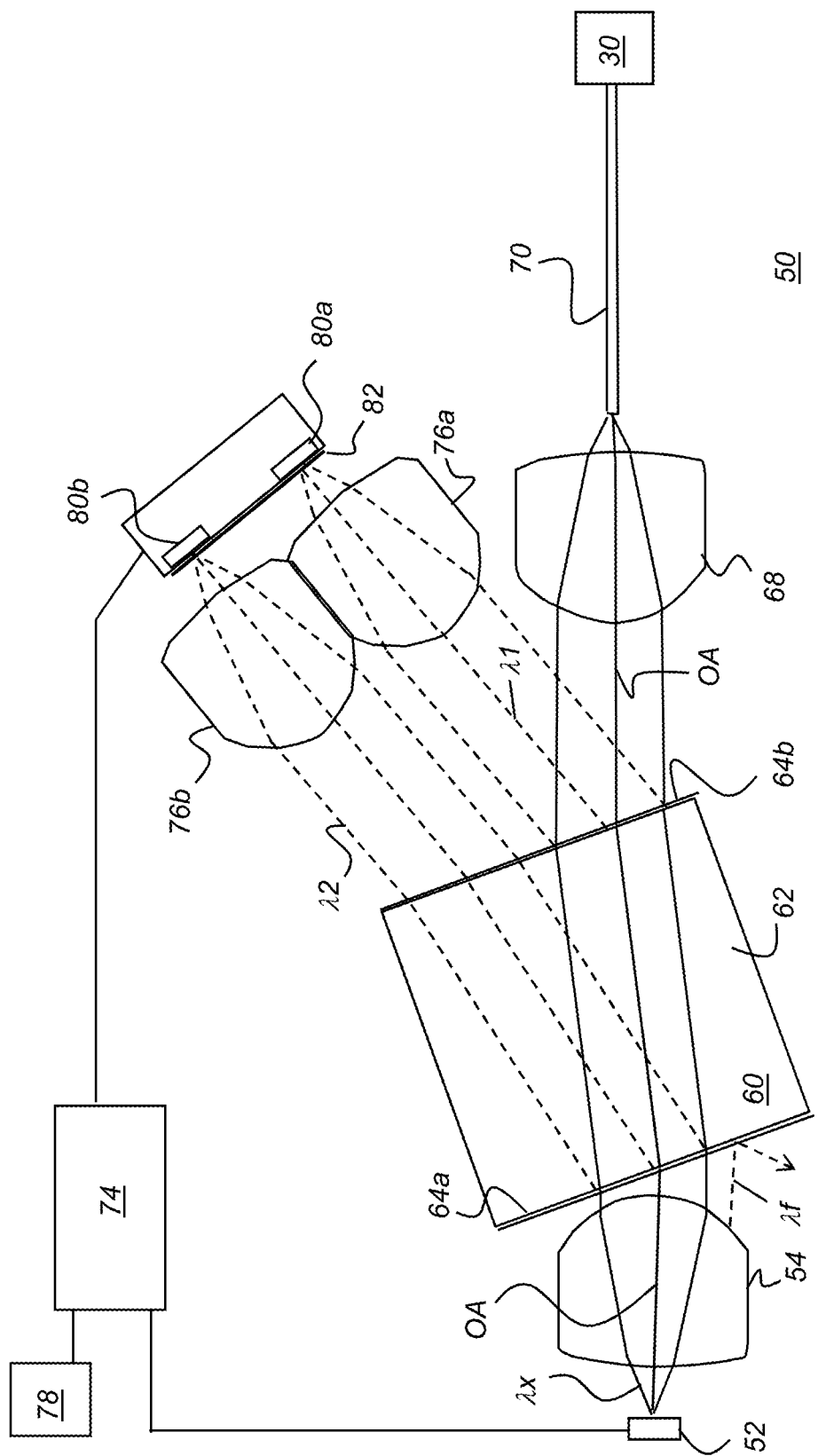
FIG. 2 is a schematic view showing a sensing apparatus according to an embodiment of the present invention.

The schematic diagram of FIG. 2 shows a sensing apparatus 50 for glucose level monitoring according to an embodiment of the present invention. Schematic diagrams of FIGS. 3A, 3B, and 3C then show the respective optical paths for light of excitation wavelength $\lambda x$, fluorescent wavelength $\lambda 1$, and fluorescent wavelength $\lambda 2$ separately, to help in describing how sensing apparatus 50 isolates and directs light of the various wavelength bands for their particular functions. In each of FIGS. 3A-3C, components that are not part of the particular optical path being described are shown in dashed outline.

Figure 3A:
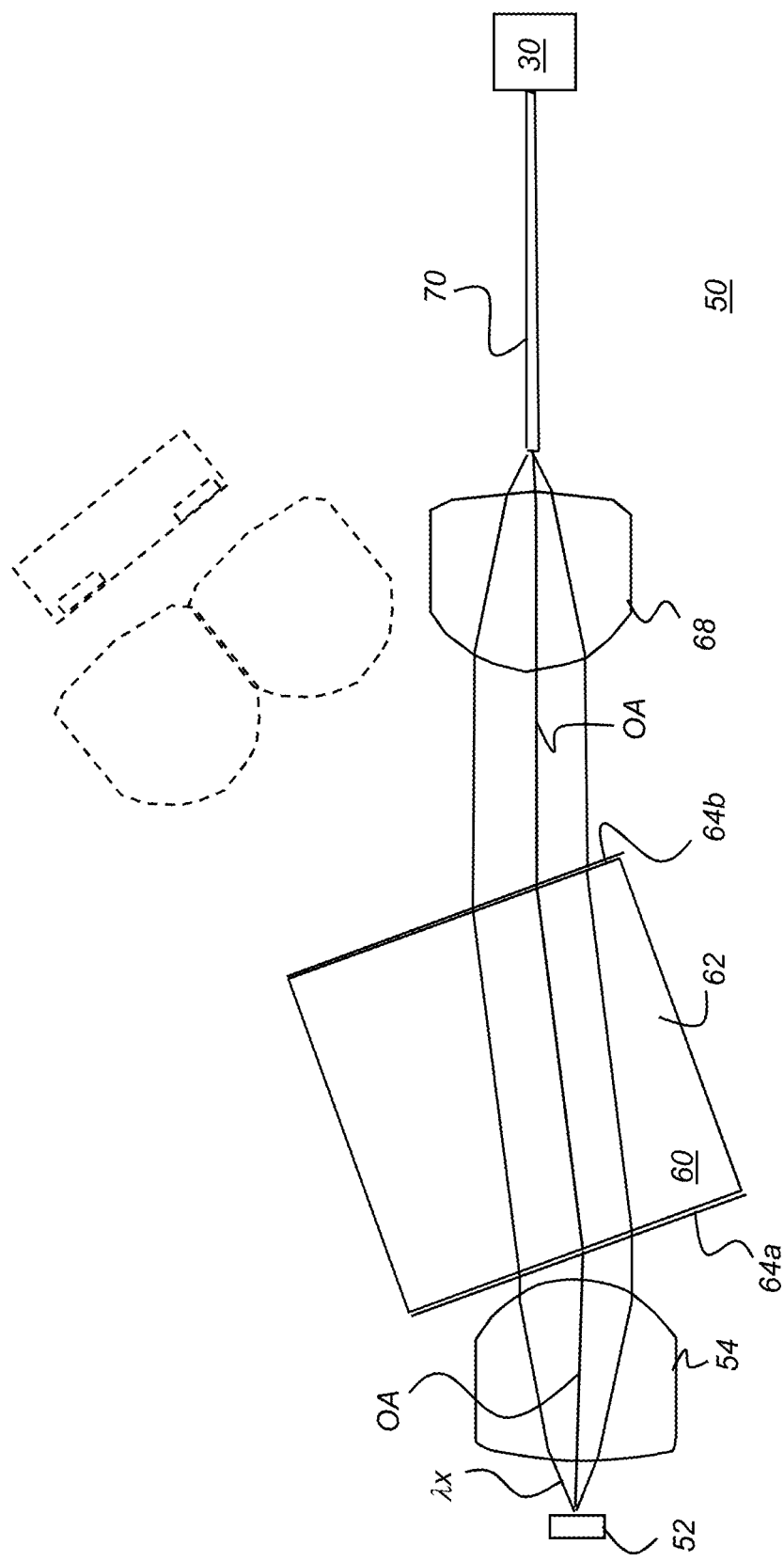
FIG. 3A shows the path of light of the excitation wavelength.

Referring to FIGS. 2 and 3A, a light source 52, such as a light-emitting diode (LED) or other solid state light source, is energizable to emit light of an excitation wavelength band $\lambda x$ along an optical axis OA. Light source 52 is in a first focal region of a collimator element 54. Collimator element 54, such as a collimating lens, conditions light from light source 52 to provide collimated light to a dichroic multiplexer 60 formed on a transparent substrate 62. Dichroic multiplexer 60 has two coated surfaces 64a and 64b, each treated or otherwise formed to transmit light of the excitation wavelength and to reflect light from fluorescence. Surfaces 64a and 64b are in parallel planes in the embodiment shown in FIG. 2, both surfaces oblique with respect to the optical axis OA. Surfaces could alternately be oblique with respect to each other. Dichroic multiplexer 60 refractively shifts the optical axis OA and transmits light of excitation wavelength band $\lambda x$ toward a focusing element 68 that is disposed to focus collimated light toward a light guide 70, such as an optical fiber, for example. Light guide 70 directs the excitation light to sample 30 and directs fluorescent light back toward focusing element 68, dichroic multiplexer 60, and detectors 80a and 80b, as described in more detail subsequently. A control logic processor 74 is in signal communication with light source 52 for switching on energizing energy to the light source and is in signal communication with detector elements 80a and 80b for measuring the light from respective fluorescent wavelengths $\lambda 2$ and $\lambda 1$ respectively. Control logic processor 74 can be any of a number of types of programmable logic control devices, such as a dedicated micro-controller, microprocessor, or computer, and may have its logic functions executed in hardware. An optional display 78 is in signal communication with the control logic processor 74 for reporting results of measured data, such as reporting a glucose reading or warning message based upon measured results according to signals obtained from detector elements 80a and 80b, for example. Control logic processor 74 can alternately be in signal communication with other devices for reporting measurement results. In addition, control logic processor 74 can be in signal communication with apparatus that inject one or more fluorophores for patient testing.

Figure 3B:
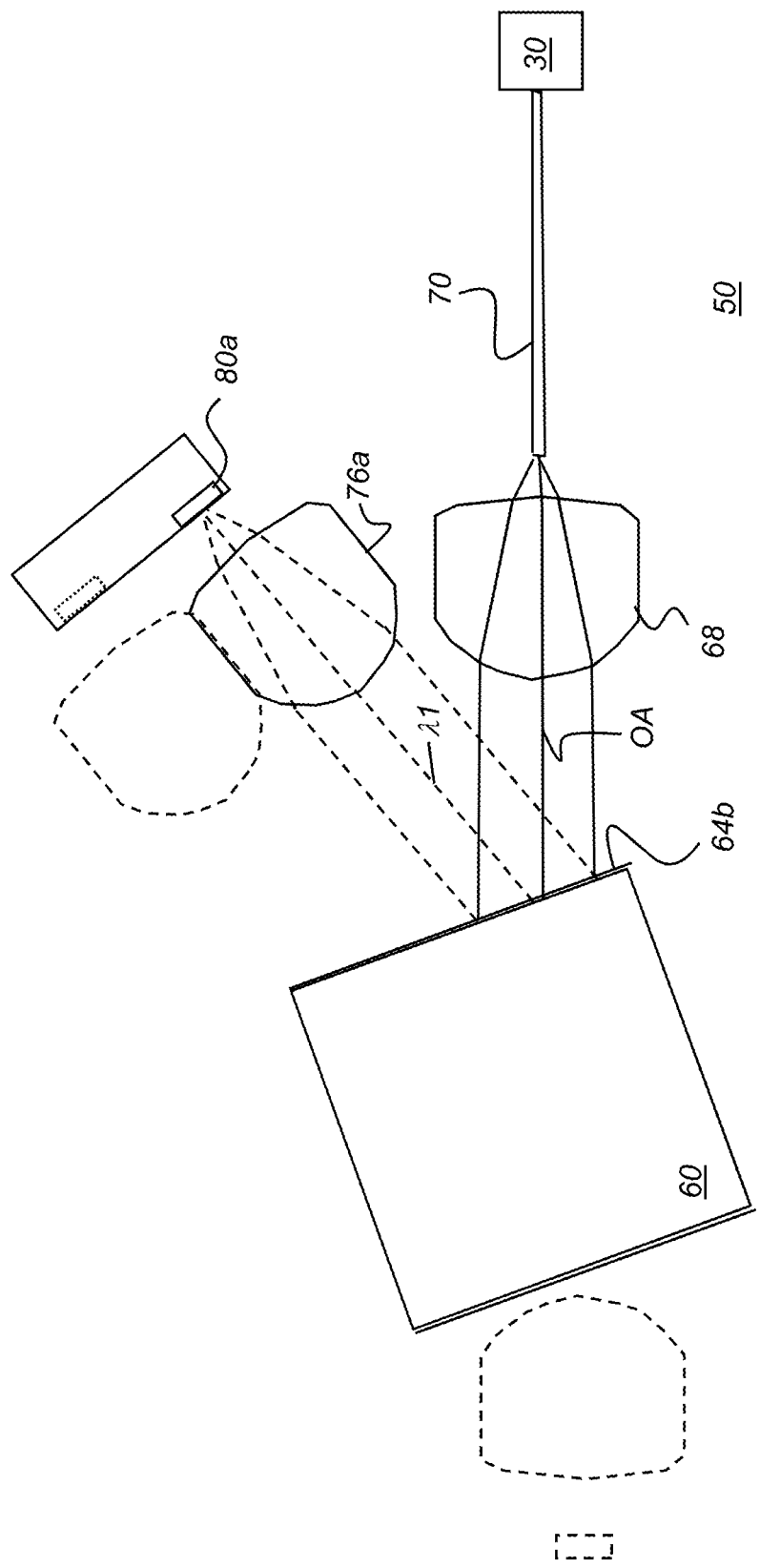
FIG. 3B shows the path of light of a first fluorescent wavelength.

Turning now to FIG. 3B, there is shown the detector path for light of first fluorescent wavelength band $\lambda 1$ in the apparatus of FIG. 2. Focusing element 68 collimates this fluoresced light obtained from light guide 70 and directs it toward coated surface 64b. The surface 64b coating is treated to transmit light of excitation wavelength $\lambda x$ and light of second fluorescent wavelength band $\lambda 2$ and to reflect light of first fluorescent wavelength band $\lambda 1$. Reflected light of first fluorescent wavelength band $\lambda 1$ is thus directed toward detector element 80a, through a focusing element 76a such as a lens.

Figure 3C:
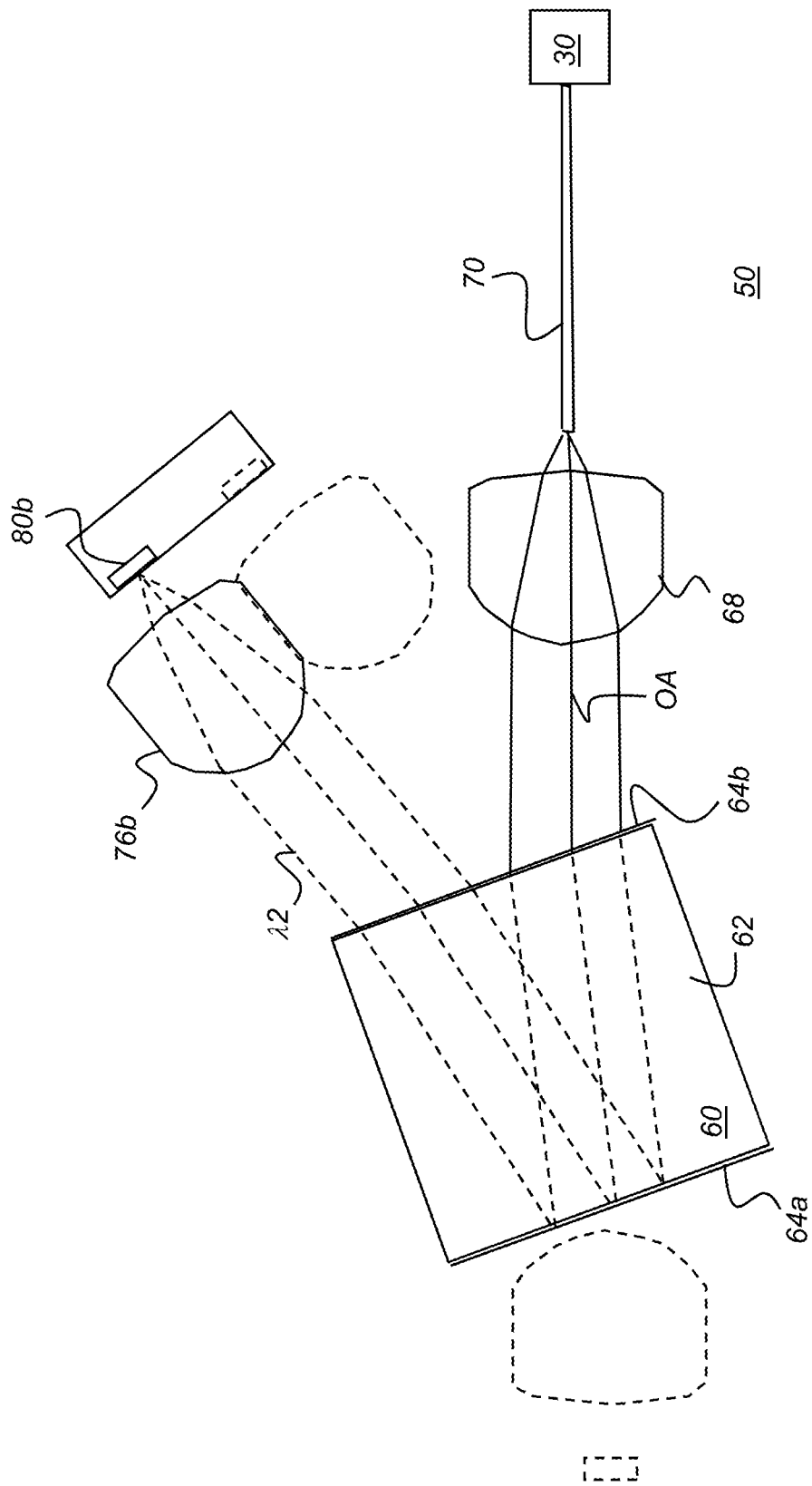
FIG. 3C shows the path of light of a second fluorescent wavelength.

FIG. 3C shows the detector path for light of second fluorescent wavelength band $\lambda 2$ in the sensing apparatus 50 of FIG. 2. Focusing element 68 collimates this fluoresced light and directs it through coated surface 64b and toward coated surface 64a. The surface 64a coating is treated to transmit light of excitation wavelength band $\lambda x$ and to reflect at least light of second fluorescent wavelength band $\lambda 2$. Reflected light of second fluorescent wavelength band $\lambda 2$ is thus directed toward detector element 80b, through a focusing element 76b. The spectral characteristic of surface 64a can be designed to transmit or to reflect any light of fluorescent wavelength $\lambda 1$ that was not reflected form surface 64b.

Detector elements 80a and 80b can have any of a number of different arrangements. FIGS. 2, 3B, and 3C show detector elements 80a and 80b as individual pixels on an integrated detector 86, such as a CMOS (complementary metal-oxide semiconductor) detector array, for example. In an alternate embodiment, detector elements 80a and 80b are separate elements, such as discrete light detectors. The size of the detector array, that is, the sensitive area available for receiving and measuring light, is preferably large, thus relaxing alignment requirements, as described in more detail subsequently. As is shown in FIG. 2, one or more optional filters 82 can be disposed in the detector path for further conditioning and isolation of the sensed light according to wavelength.

Figure 4:
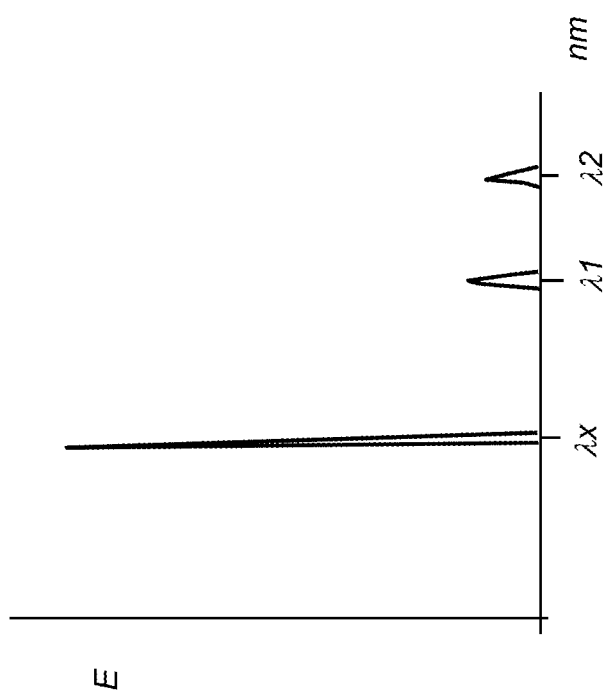
FIG. 4 is a graph that schematically represents how emitted wavelength bands relate to the excitation wavelength light.

The graph of FIG. 4 shows, in exaggerated, conceptual form and not to scale, the respective energy levels E and wavelength bands for excitation wavelength $\lambda x$ and first and second fluorescent wavelengths $\lambda 1$ and $\lambda 2$ in an exemplary embodiment. As is shown in this graph, the energy of the excitation light at wavelength $\lambda x$ far exceeds the energy levels of the fluorescent light that is obtained from the sample. Thus, it can be appreciated that the optical system must suppress excitation light at wavelength $\lambda x$ from the detection path. This isolation of wavelengths is largely a function of dichroic coatings on surfaces 64a and 64b (FIG. 2), preventing stray light from light source 52 from inadvertently reaching detector elements 80b and 80a.

In addition, because signal levels for first and second fluorescent wavelengths $\lambda 1$ and $\lambda 2$ are relatively low, random fluorescence from within the optical system must be suppressed or removed. Fluorescence can occur, for example, from within lenses or other components and may be at measurable levels from some glass or plastic optical materials, for example. Fluoresced light is generally at longer wavelengths than the excitation light. Thus, proper specification of dichroic coatings on surfaces 64a and 64b helps to keep this stray fluoresced light from the detection path. Referring back to FIG. 2, stray fluorescent light $\lambda f$ that is generated from within collimator element 54 is reflected from surface 64a and thus removed from the optical system.

In embodiments of the present invention, optical coatings design is simplified by conditioning each of the light paths to provide collimated light. This narrows the range of incident angles for the light at each of coated surfaces 64a and 64b, so that coatings design can be performed without concern for response changes of thin film coatings that typically occur when light is incident over a broad angular range.

Fluorescence from within dichroic multiplexer 60 is reduced by using fused silica or other substrate 62 that exhibits negligible fluorescence to the excitation light at wavelength λx.

Figure 5:
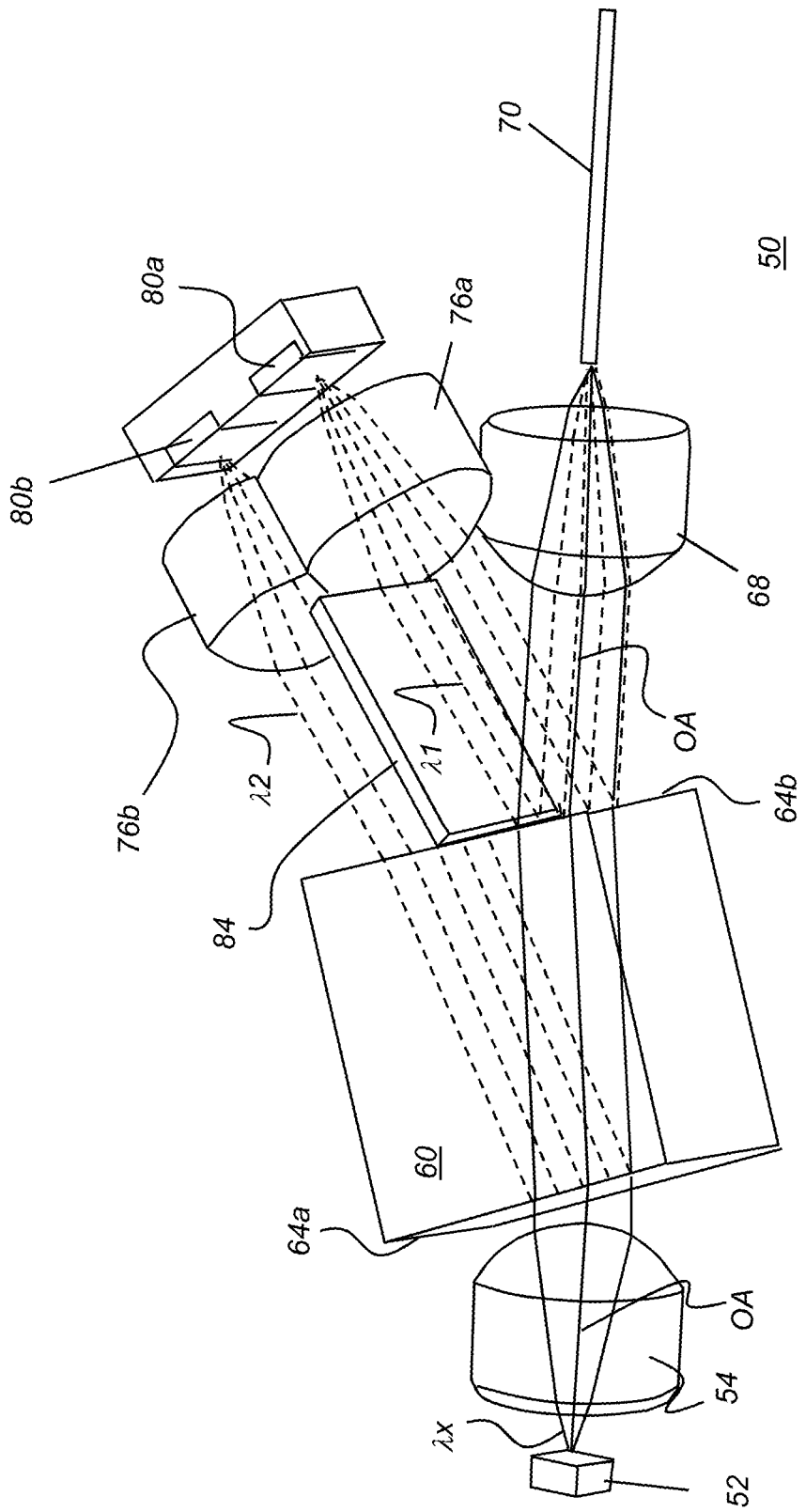
FIG. 5 is a perspective view of a sensing apparatus showing an optional baffle element.

A number of optional components and alternate arrangements can be provided for improving the performance of sensing apparatus 50 or for adapting the design to be more compact. FIG. 5 is a perspective view of a sensing apparatus showing an optional baffle element 84. Baffle element 84 helps to isolate the respective light paths for light of fluorescent wavelengths λ1 and λ2 and thus to prevent crosstalk effects. Baffle element 84 could alternately be positioned closer to detector elements 80*a* and 80*b*. One or more additional filters could alternately be used in addition to baffle element 84. In the particular example embodiment shown in FIG. 5, surfaces 64*a* and 64*b* are oblique to each other, which can be advantageous for more compact packaging.

Figure 6:
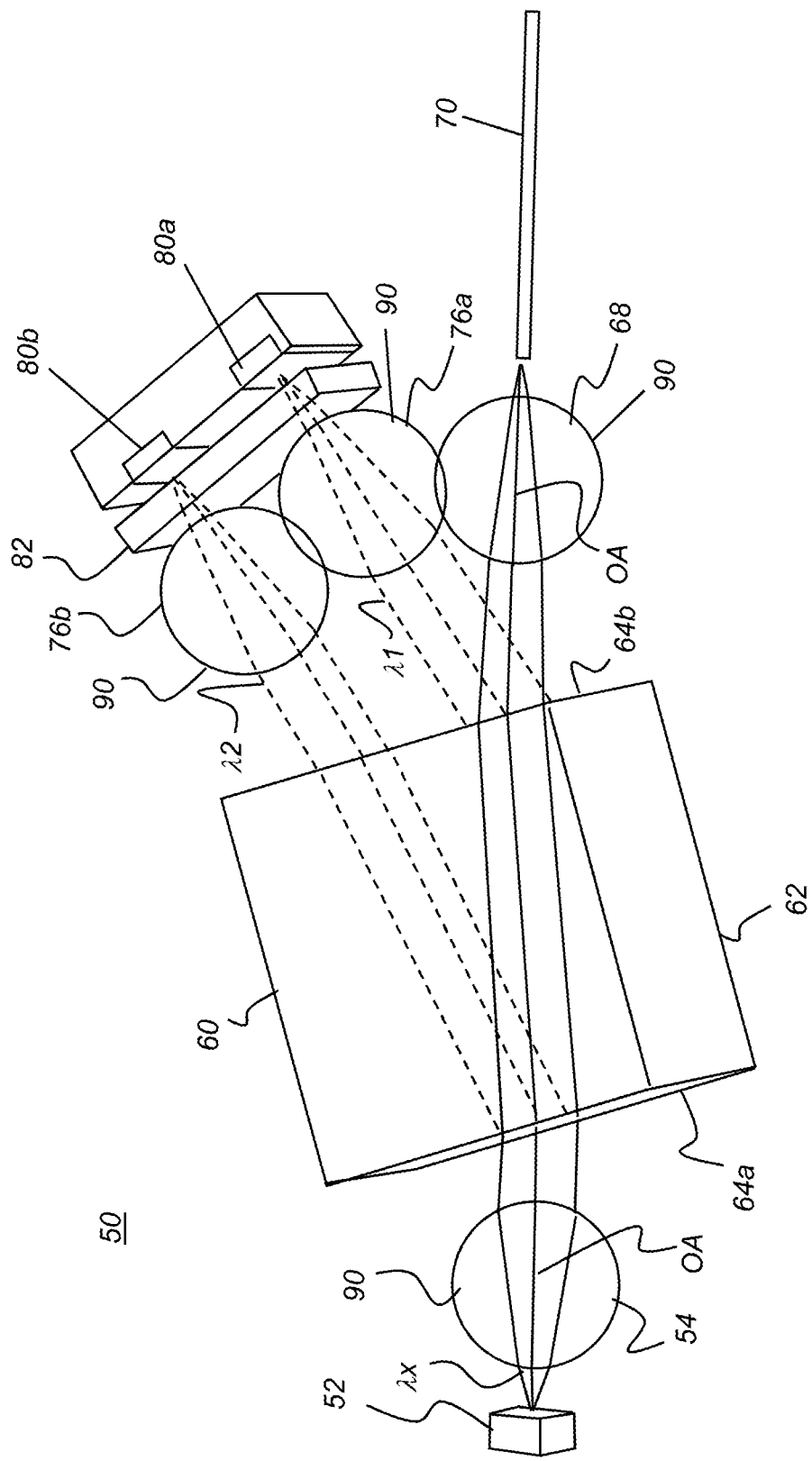
FIG. 6 is a perspective view of an alternate embodiment of the present invention using ball lenses for conditioning the excitation and fluorescent light beams.

FIG. 6 is a perspective view of an alternate embodiment of the present invention using ball lenses 90 for conditioning and directing the excitation and fluorescent light beams. Ball lenses 90 help to provide more compact packaging and further reduce the cost of the system. Collimating lenses 54 and 68 or lenses 76*a* and 76*b* can alternately be aspheric lenses, ball lenses, or gradient index lenses. Ball lenses have been employed in other optical devices for specialized optical functions, particularly miniaturized ball lenses for use in fiber optics coupling and transmission applications. Because these devices are essentially spheres and need no adjustment, they are advantaged for low cost and ease of positioning in manufacture of an optical assembly.

Figure 7:
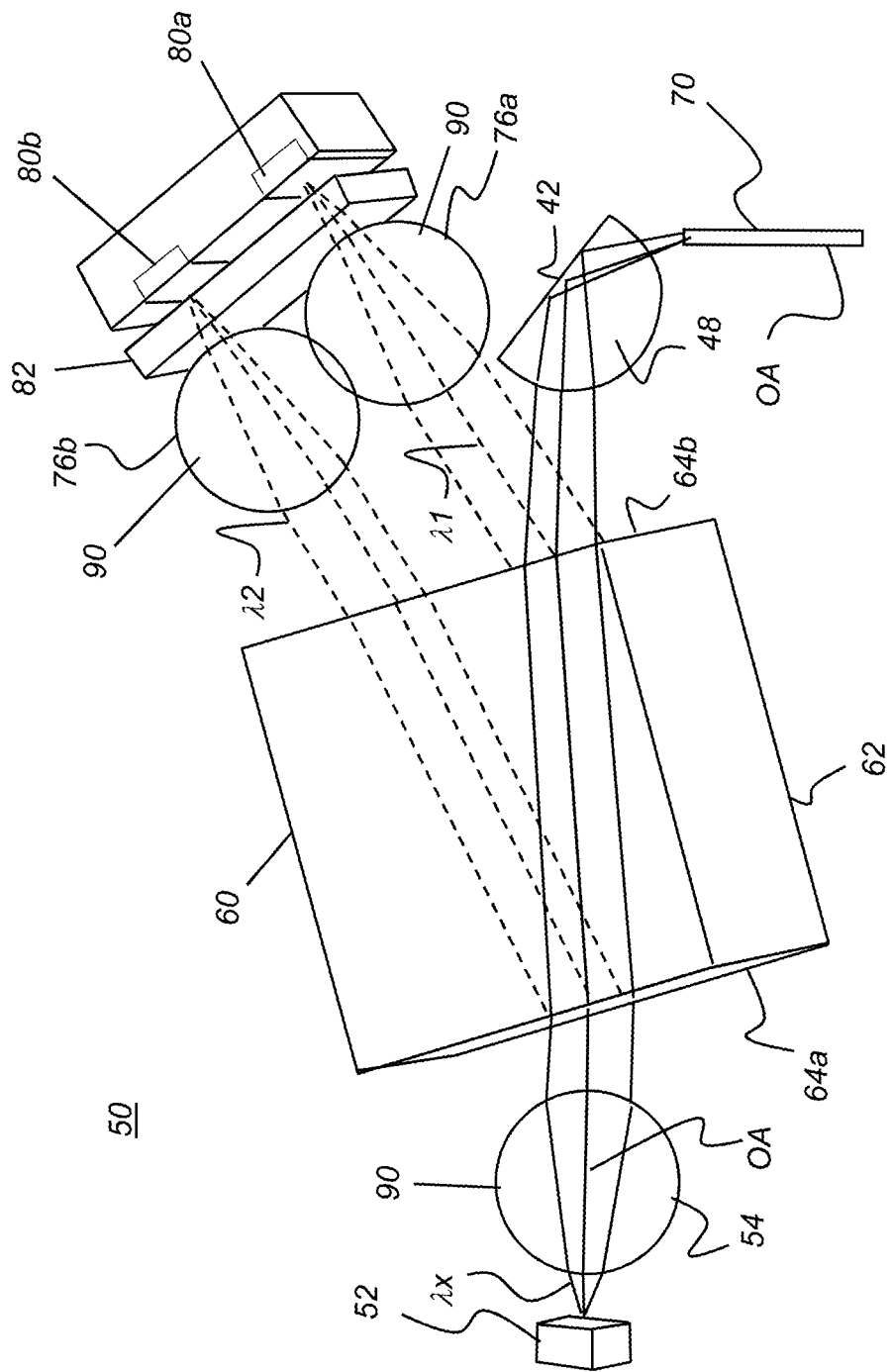
FIG. 7 is a perspective view of another alternate embodiment of the present invention using ball lenses and lens elements having reflective surfaces for conditioning the excitation and fluorescent light beams.

The perspective view of FIG. 7 shows another alternate embodiment that has a number of ball lenses 90 and also uses a hemispheric focusing element 48 that has an associated reflective surface 42. Reflection at surface 42 enables the optical axis OA to be redirected out of the plane of sensing apparatus 50 components, such as orthogonal to the plane, while still maintaining its compact overall design.

Figure 8:
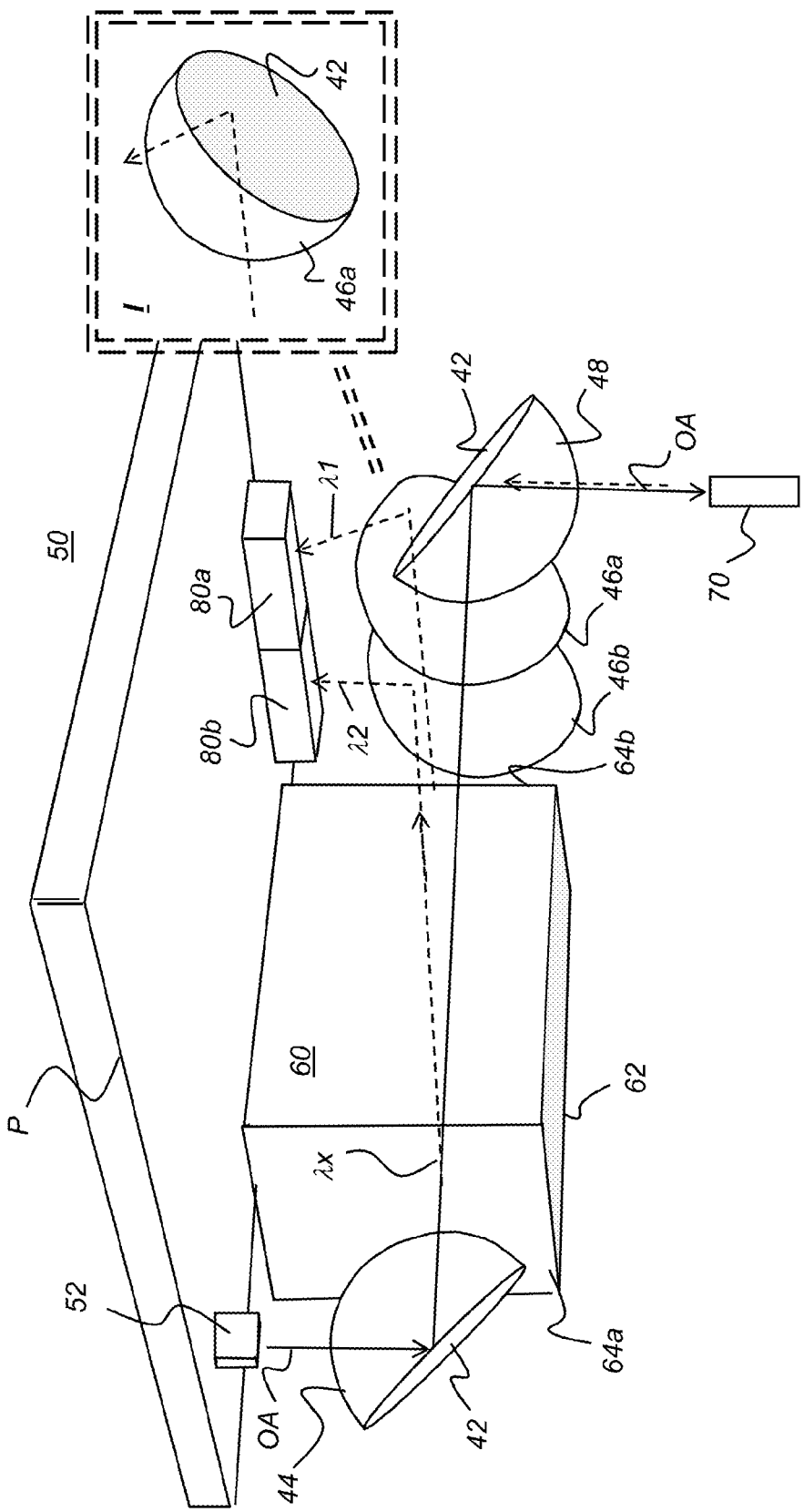
FIG. 8 is a perspective view of yet another alternate embodiment of the present invention using lens elements having reflective surfaces for conditioning the excitation and fluorescent light beams.

The perspective view of FIG. 8 uses a number of refractive and reflective focusing elements in an arrangement that allows light source 52 and detector elements 80*a* and 80*b* to be disposed within the same plane P. Collimator element 44 has a refractive portion backed by reflective surface 42 for folding optical axis OA through multiplexer 60 and toward focusing element 48. Focusing element 48, in turn, has reflective surface 42 that again folds the OA toward light guide 70. In addition, each of focusing elements 46*a* and 46*b* also has a corresponding reflective surface 42, as indicated in an inset I for focusing element 46*a*. The use of combined reflective and refractive devices in this way can help to reduce the dimensional footprint of sensing apparatus 50. This makes it possible to form a small, lightweight glucose monitor or other sensing device with inexpensive optical components. Reflective surface 42 can be a thin-film dichroic coating or a standard mirror surface.

Alignment

Embodiments of the present invention allow relaxed alignment tolerances when contrasted with conventional fluorescence sensing systems. Dichroic surface alignment is simplified by forming surfaces 64*a* and 64*b* as coatings on a transparent substrate. These surfaces are in parallel in a number of the embodiments shown herein. In an alternate embodiment, the coated surfaces 64*a* and 64*b* are oblique with respect to each other. Mounting is simplified by forming coated surfaces 64*a* and 64*b* on a transparent block, which can easily be fixtured into position.

Alignment is also facilitated by over-filling light guide 70. Consistent with an embodiment of the present invention, light source 52 is an LED whose optical etendue far exceeds the etendue of light guide 70, typically an optical fiber. This relaxes alignment requirements for both collimator element 54 and focusing element 68 (or 48), since the imaged LED area exceeds the small input aperture of the optical fiber of light guide 70.

In a similar way, alignment is facilitated by providing detector elements 80*a* and 80*b* of sufficient size so that precise focus of the sensed light onto the detectors is not necessary and relatively loose tolerances can be provided.

For glucose measurement, light guide 70, an optical fiber, is in optical communication with fluorophores in interstitial fluid of the patient being monitored, such as by connection through a hypodermic needle, for example. The sensing apparatus can work in unison with monitoring apparatus that inject the fluorophores for measurement and report results to the patient or other monitoring party.

Embodiments of the present invention provide a sensing apparatus for glucose monitoring or other functions that provides straightforward alignment, compact parts positioning, and favorable signal-to-noise characteristics. Stray fluorescence can be effectively eliminated from the signal detection path. The sensing apparatus is capable of measuring energy in two different fluorescent wavelength bands and can provide results on the ratio of energy in the two respective wavelength bands. These results can be displayed or provided as a signal or data to another apparatus or system, for example.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, various types of light source could be used, including solid state light sources such as an LED or a laser. One or more light sources could be provided. Lenses or other optical components, such as concave mirrors or other curved reflective devices, can be employed for providing focused and collimated light, with corresponding changes to the optical path. One or more reflective surfaces can be provided for folding the optical path, such as at the light source, for example. Results from detector element measurements and any subsequent calculation can be displayed or otherwise reported, such as by an audible beep or other signal or by wired or wireless transmission to a networked computer or other signal recipient. In the case of glucose monitoring, a signal from a sensing apparatus of the present invention could be used to actuate an automated dosage administration device, for example.

Thus, what is provided is an apparatus and method for providing excitation light to a sample and sensing fluorescent light of different wavelengths from the sample.

The invention claimed is:

1. A sensing apparatus for detecting light of a first fluorescent wavelength band and light of a second fluorescent wavelength band from a sample, the apparatus comprising:
   a light source energizable to generate a light of an excitation wavelength and disposed along an optical axis in a first focal region of a first collimator element;
   a dichroic multiplexer formed on a transparent substrate and comprising:
      (i) a first coated surface oblique to the optical axis and treated to transmit light of the excitation wavelength and to reflect light of at least the second fluorescent wavelength band;
      (ii) a second coated surface spaced apart from the first coated surface and treated to transmit light of the excitation wavelength and of the second fluorescent wavelength band and to reflect light of the first fluorescent wavelength band;

a focusing element disposed to focus the light of the excitation wavelength toward a light guide and to direct collimated light of the first fluorescent wavelength band and collimated light of the second fluorescent wavelength band from the light guide to the dichroic multiplexer;

a first detector element in the path of reflected light of the first fluorescent wavelength band from the second coated surface;

and a second detector element in the path of reflected light of the second fluorescent wavelength band from the first coated surface.

2. The sensing apparatus of claim 1 wherein the first and second coated surfaces are parallel to each other.

3. The sensing apparatus of claim 1 wherein the first and second coated surfaces are obliquely disposed with respect to each other.

4. The sensing apparatus of claim 1 wherein the transparent substrate is fused silica.

5. The sensing apparatus of claim 1 wherein the light source is a solid-state light source.

6. The sensing apparatus of claim 1 wherein one or more of the focusing element or the first collimator is a ball lens.

7. The sensing apparatus of claim 1 wherein the light guide comprises an optical fiber.

8. The sensing apparatus of claim 1 further comprising a baffle between the path of reflected light of the first fluorescent wavelength band and reflected light of the second fluorescent wavelength band.

9. The sensing apparatus of claim 1 wherein the first collimator element is taken from the group consisting of an aspheric lens, a ball lens, a gradient index lens, and a concave mirror.

10. The sensing apparatus of claim 1 further comprising a first focusing lens in the path of reflected light of the first fluorescent wavelength band.

11. The sensing apparatus of claim 10 wherein the first focusing lens comprises a reflective surface.

12. The sensing apparatus of claim 1 wherein one or more of the focusing element or the first collimator element further comprise a reflective surface for folding the optical axis.

13. A glucose level sensing apparatus comprising:

a light source energizable to generate a light of an excitation wavelength and disposed along an optical axis in a first focal region of a first collimator element;

a dichroic multiplexer formed on a transparent substrate and comprising:
  (i) a first coated surface oblique to the optical axis and treated to transmit light of the excitation wavelength and to reflect light of at least the second fluorescent wavelength band;
  (ii) a second coated surface parallel to the first coated surface and treated to transmit light of the excitation wavelength and of the second fluorescent wavelength band and to reflect light of the first fluorescent wavelength band;

a focusing element disposed to focus the light of the excitation wavelength toward a light guide to the sample, and to direct collimated light of the first fluorescent wavelength band and collimated light of the second fluorescent wavelength band from the light guide to the dichroic multiplexer;

a first detector element in the path of reflected light of the first fluorescent wavelength band from the second coated surface;

a second detector element in the path of reflected light of the second fluorescent wavelength band from the first coated surface;

and a control logic processor in signal communication with the light source and with the first and second detector elements and further in signal communication with a display device for displaying a result according to measurements obtained from the first and second detector elements.

14. The sensing apparatus of claim 13 wherein the first and second coated surfaces are parallel to each other.

15. The sensing apparatus of claim 13 wherein the first and second coated surfaces are obliquely disposed with respect to each other.

16. The sensing apparatus of claim 13 wherein the transparent substrate is fused silica.

17. The sensing apparatus of claim 13 wherein the light source is a solid-state light source.

18. The sensing apparatus of claim 13 wherein one or more of the focusing element or the first collimator is a ball lens.

19. The sensing apparatus of claim 13 wherein the light guide comprises an optical fiber.

20. A method for detecting light of a first fluorescent wavelength band and light of a second fluorescent wavelength band from a sample, the method comprising:

energizing a solid state light source and directing collimated light of an excitation wavelength along an optical axis toward a dichroic multiplexer that is formed on a transparent substrate and that comprises:
  (i) a first coated surface oblique to the optical axis and treated to transmit light of the excitation wavelength and to reflect light of the second fluorescent wavelength band;
  (ii) a second coated surface spaced apart from the first coated surface and treated to transmit light of the excitation wavelength and of the second fluorescent wavelength band and to reflect light of the first fluorescent wavelength band;

focusing the light of the excitation wavelength toward a light guide to the sample, and directing light of the first fluorescent wavelength band and light of the second fluorescent wavelength band from the light guide to the dichroic multiplexer;

obtaining a first signal from a first detector element in the path of light of the first fluorescent wavelength band reflected from the second coated surface of the dichroic multiplexer;

obtaining a second signal from a second detector element in the path of light of the second fluorescent wavelength band reflected from the first coated surface of the dichroic multiplexer;

and displaying a result according to the obtained first and second signals.

* * * * *